United States Patent [19]

Saito et al.

[11] Patent Number: 5,817,492
[45] Date of Patent: Oct. 6, 1998

[54] RECOMBINANT DNA VIRAL VECTOR FOR TRANSFECTING ANIMAL CELLS

[75] Inventors: Izumu Saito; Yumi Kanegae, both of Tokyo, Japan

[73] Assignee: Sumitomo Pharmaceuticals Company, Ltd., Osaka, Japan

[21] Appl. No.: 521,575

[22] Filed: Aug. 30, 1995

[30] Foreign Application Priority Data

Sep. 19, 1994 [JP] Japan .................................. 6-251312

[51] Int. Cl.⁶ .......................... A61K 48/00; C12N 15/00
[52] U.S. Cl. ................................... 435/172.3; 435/240.1; 435/240.2; 435/320.1; 435/240.21; 514/44; 424/93.21
[58] Field of Search ................. 514/44, 2, 8; 435/320.1, 435/69.1, 172.3, 240.1, 240.2; 536/23.1, 24.1; 424/93.21

[56] References Cited

FOREIGN PATENT DOCUMENTS

| A0220009 | 4/1987 | European Pat. Off. |
| 0300422 | 1/1989 | European Pat. Off. |
| A0300422 | 1/1989 | European Pat. Off. |
| 0542466 | 5/1993 | European Pat. Off. |
| 0732405 | 9/1996 | European Pat. Off. |
| 2737501 | 2/1997 | France |
| WO9640955 | 12/1996 | WIPO |

OTHER PUBLICATIONS

Proceedings of the National Academy of Sciences of USA, vol. 84, No. 24, 1 Dec. 1987, pp. 9108–9112, XPo02002088 Sauer, B. et al: "Site–Specific Insertion of DNA Into a Pseudorabies Virus Vector".
Journal of Virology, vol. 66, No. 9, 1 Sep. 1992, pp. 5509–5515, XP000568386 Gage P.J. et al: "A Cell–free Recombination System for Site–Specific Integration of Multigenic Shuttle Plasmids Into the Herpes Simplex Virus Type 1 Genome".
Mollecular and Cellular Biology, vol. 13, No. 2, Feb. 1993, Washington US, pp. 918–927, XP00202619, Wang, Q. & Taylor, M.W.: "Correction of a deletion mutant by gene targeting with an adenovirus vector".
Nucleic Acids Research, vol. 23, No. 19, 11 Oct. 1995, pp. 3816–3821, XP002011774 Kanegae, Y. et al: "Efficient Gene Activation in Mammalian Cells by using Recombinant Adenovirus Expressing Site–Specific CRE Recombinase".
Fukushige et al., PNAS, 89, 1992, 7905–7909.
Sauer et al., Nuc. Acids Res., 17(1), 1989, 147–160.
Hodgson, Exp. Opin. Ther. Pat., 5(5), 1995, 459–468.
Culver et al., TIG, 10(5), 1994, 174–178.
Miller et al., FASEB Journal, 9, 1995, 190–199.
Marshall, Science, 269, 1995, 1050–1055.
NIH, "Report and Recommendations . . . ", Orkin et al. Dec. 7, 1995, 1–40.

Niwa et al, "Efficient Selection for High–Expression Transfectants with a Novel Eukaryotic Vector," *Gene*, 108, pp. 193–200 (1991).
Engelhardt et al, "Direct Gene Transfer of Human CTFR Into Human Bronchial Epithelia of Xenografts with El–Deleted Adenoviruses,"0 *Nature Genetics*, vol. 4, pp. 27–34 (May 1993).
Saito et al, "Adenovirus Vector," The 41st General Meeting: The Society of Japanese Virologists (1993).
Kanegae et al "Adenovirus Vector and Gene Therapy," *Experimental Medicine*, vol. 12, No. 3 (1994).
Kanegae et al, Experimental Medicine Supplemental Volume, Biomanual Series 4, pp. 43–58 (1994).
Kanegae et al., "Efficient Gene Activation . . . Recombinase, "Nucleic Acids Research, vol. 23, No. 19, pp. 3816–3821 (1995).
Bergemann et al., "Excision of Specific DNA . . . Recombination," Nucleic Acids Research, vol. 23, No. 21, pp. 4451–4456 (1995).
The 43rd Annual Meeting of the Society of Japanese Virologists, (Sep. 29, 1995), 2016, p.126.
*Science*, vol. 265, Jul. 1, 1994, pp. 103–106, Hua Gu et al, "Deletion of a DNA Polymerase β Gene Segment in T Cells Using Cell Type–Specific Gene Targeting".
*Journal of Virology*, Aug. 1995, pp. 4600–4606, Martina Anton et al, "Site–Specific Recombination Mediated by an Adenovirus Vector Expressing the Cre Recombinase Protein: a Molecular . . . Expression".
*The First Annual Meeting 1995, Japanese Society of Gene Therapy*, May 21, 1995, Yumi Kanagae et al, "Application of Cre/loxP Sysem to Adenovirus Vector".
*The Second Brain Tumor Gene Therapy Meeting*, Feb. 3 and 4, 1995, "Adenovirus Vector".

*Primary Examiner*—Jacqueline M. Stone
*Assistant Examiner*—Andrew Milne
*Attorney, Agent, or Firm*—Sughrue, Mion, Zinn, Macpeak & Seas, PLLC

[57] ABSTRACT

An animal cell is co-transfected with both a recombinant DNA viral vector which bears a promoter, a recombinase gene and a poly(A) sequence and a recombinant DNA viral vector which bears two recombinase-recognizing sequences and which further bears an origin of replication, a promoter, a foreign gene and a poly(A) sequence, each of which is located between the two recombinase-recognizing sequences. Thereafter, in the co-transfected animal cell, a DNA fragment containing the origin of replication, promoter, foreign gene and poly(A) sequence is excised from the vector by the action of a recombinase expressed in the another vector. The DNA fragment forms a circular DNA molecule which autonomously replicates in the co-transfected animal cell due to the origin of replication, whereby the foreign gene is continuously expressed. Accordingly, the combination of the above two DNA viral vectors wherein a gene which is defective in patients is used as the foreign gene is quite useful especially for the treatment of the patient with hereditary diseases.

15 Claims, 1 Drawing Sheet

RECOMBINANT DNA VIRAL VECTOR FOR TRANSFECTING ANIMAL CELLS

BACKGROUND OF THE INVENTION

1. Field of the Invention

The present invention relates to a recombinant DNA viral vector for transfecting an animal cell. More particularly, the present invention relates to a recombinant DNA viral vector comprising a recombinase gene or a DNA sequence coding for a recombinase-recognizing sequence, a method for transducing a foreign gene into an animal cell using said vector, and use thereof in gene therapy.

2. Related Art Statement

A retrovirus has often been employed as a viral vector for gene transduction. However, a retrovirus is transfected only into mitotic cells and integrated into a chromosome of host cells. A retrovirus as a viral vector, therefore, encounters a problem from the viewpoint of safety, especially in gene therapy. It is thus considered that a retrovirus should be limitedly used as a viral vector.

An adenoviral vector is advantageous in that it shows a transducing efficiency of almost 100% in a variety of animal cultured cells, has no positive mechanism for integration into the chromosome unlike retrovirus, and can transduce a gene even into a resting cell. In view of such advantages, an adenoviral vector is considered as being applicable over an extremely wide fields for attempting to transduce a foreign gene. It would thus be established in the near future that an adenoviral vector be used as one of major technology for gene therapy.

An adenovirus vector has been widely utilized as one technology for gene therapy or for researching an expression in highly differentiated cells such as a nervous system cell. In vivo gene therapy has been extensively studied wherein a gene which is defective in a living cell is transduced into the cell by direct injection of the gene into a tissue in which the cell exists. In the United States, five research groups have already been allowed to conduct clinical trials for treating patients with cystic fibrosis by the in vivo gene therapy. Furthermore, research with gene therapy has also been extended to muscular dystrophy, familial hypercholesterolemia, and brain tumors. An adenoviral vector enables transduction of a gene even into a resting cell. Therefore, an adenoviral vector has been utilized for transduction of a gene into differentiated cells, especially into a nervous system cell, when conducting experiments on gene transduction into a primary culture cell or animal body.

In view of the foregoing, it is highly expected that an adenoviral vector introduced into practice particularly in gene therapy, because the vector enables an expression of a gene by direct injection or administration into an animal body, as well as transduction of a gene into various differentiated and non-differentiated cells including a nervous system cell.

Unlike a retrovirus, an adenoviral vector lacks any positive mechanism for integration into the chromosome. As a result, expression of a gene in the vector occurs only temporarily. That is, the expression continues only for a few weeks, at most for about 2 months. Thus, when the therapeutic effect has to be maintained, the injection or administration of the vector should be repeated for the continuous expression. However, the repeated injections or administrations might induce the generation of an antibody reducing the therapeutic effect.

SUMMARY OF THE INVENTION

An object of the present invention is to provide a recombinant adenoviral vector system wherein a foreign gene is transduced into an animal cell by an adenoviral vector and then converted into a form capable of autonomously replicating within the cell. A further object of the present invention is to provide such a system for gene therapy.

In order to achieve the foregoing objects, the present inventors have conducted extensive research and succeeded in obtaining a recombinant adenoviral vector system:

wherein an expression unit bearing a foreign gene is transduced into cells with an adenoviral vector, and then converted into a circular DNA molecule by the use of a recombinase gene and a recombinase-recognizing sequence and, wherein a replication origin has been further introduced into the thus formed circular DNA molecule, whereby the gene expression unit bearing the foreign gene is capable of autonomously replicating to continue expressing the foreign gene in the cells.

Herein, the term "a recombinase" refers to a specific recombination DNA enzyme, which is capable of recognizing a specific DNA sequence composed of several tens of base pairs to cleave the sequence and relegate the DNA fragments formed from such cleavages therewith to produce a new DNA sequence. Accordingly, both a recombinant adenoviral vector expressing the recombinase and a recombinant adenoviral vector having two copies of the recombinase-recongnizing sequence at the same orientation are constructed, and both vectors are co-transfected into a cell, wherein the recombinase is expressed in the vector to cleave the two recombinase-recognizing sequences in the vector followed with reconstruction to produce a circular DNA molecule formed from a DNA fragment which has existed between the two recombinase-recognizing sequences and has been cut off from the vector with the recombinase. Therefore, where such a DNA fragment has an expression unit having a foreign gene and an origin of replication introduced therein, the DNA fragment autonomously replicates after being converted into a circular DNA molecule, and is permanently maintained in the cell to continue to express the foreign gene. Thus, if such a recombinant adenoviral vector system is applied to gene therapy, a therapeutic effect is enabled over a long period of time, by a single injection or administration of such vectors.

On these new findings, further investigations have been made to accomplish the present invention.

Accordingly, an object of the present invention is to provide a recombinant DNA viral vector (1) for transfecting an animal cell, comprising a promoter, a recombinase gene and a poly(A) sequence.

Another object of the present invention is to provide a recombinant DNA viral vector (2) according to the above vector (1), wherein said DNA viral vector is an adenoviral vector.

Further, another object of the present invention is to provide a recombinant DNA viral vector (3) according to the above vector (2), wherein said recombinase gene is recombinase Cre gene derived from *E. coli* P1 phage.

Further, another object of the present invention is to provide a recombinant DNA viral vector (4) for transfecting an animal cell, comprising two recombinase-recognizing sequences, an origin of replication which is operable in the animal cell, a promoter, a foreign gene and a poly(A) sequence, all of said origin of replication, promoter, foreign gene and poly(A) sequence being located between the two recombinase-recognizing sequences.

Further, another object of the present invention is to provide a recombinant DNA viral vector (5) according to the above vector (4), wherein said DNA viral vector is an adenoviral vector.

Further, another object of the present invention is to provide a recombinant DNA viral vector (6) according to the vector (5), wherein said origin of replication, promoter, foreign gene and poly(A) sequence are located in this order from the upstream one of the two recombinase-recognizing sequences.

Further, another object of the present invention is to provide a recombinant DNA viral vector (7) according to the above vector (5), wherein said foreign gene, poly(A) sequence, origin of replication, and promoter are located in this order from the upstream one of the two recombinase-recognizing sequences.

Further, another object of the present invention is to provide a recombinant DNA viral vector (8) according to any one of the above vectors (4) through (7), wherein said recombinase-recognizing sequence is a DNA sequence encoding loxP which is a substrate for recombinase Cre.

Further, another object of the present invention is to provide a recombinant DNA viral vector (9) according to any one of the above vectors (4) through (8), wherein said origin of replication is derived from virus or animal cell.

Further, another object of the present invention is to provide a recombinant DNA viral vector (10) according to the above vector (9), wherein said origin of replication is selected from the group consisting of origins of replication derived from papovavirus, herpes virus, adenovirus, pox virus and parvovirus.

Further, another object of the present invention is to provide a recombinant DNA viral vector (11) according to any one of the above vectors (1) through (10), wherein said promoter and poly(A) sequence are involved in a hybrid promoter (CAG promoter) comprising a cytomegalovirus enhancer, a chicken β-actin promoter, and a rabbit β-globin splicing acceptor and poly(A) sequence.

Further, another object of the present invention is to provide a method (12) for transducing a foreign gene into an animal cell which comprises the steps of:

co-transfecting the animal cell with both a recombinant DNA viral vector comprising a promoter, a recombinase gene and a poly(A) sequence, and a recombinant DNA viral vector comprising two recombinase-recognizing sequences, an origin of replication which is operable in the animal cell, a promoter, a foreign gene and a poly(A) sequence, all of said origin of replication, promoter, foreign gene and poly(A) sequence being located between the two recombinase-recognizing sequences;

cutting off a DNA fragment containing said origin of replication promoter, foreign gene and poly(A) sequence to produce a circular DNA molecule; and, autonomously replicating said circular DNA molecule within the co-transfected animal cell.

Further, another object of the present invention is to provide a method (13) for transducing a foreign gene into an animal cell according to the above method (12), wherein each of said two DNA viral vectors is an adenoviral vector.

Further, another object of the present invention is to provide a method for transducing a human gene into a cell which comprises using the above method (12) or (13) in a gene therapy.

Figure 1:
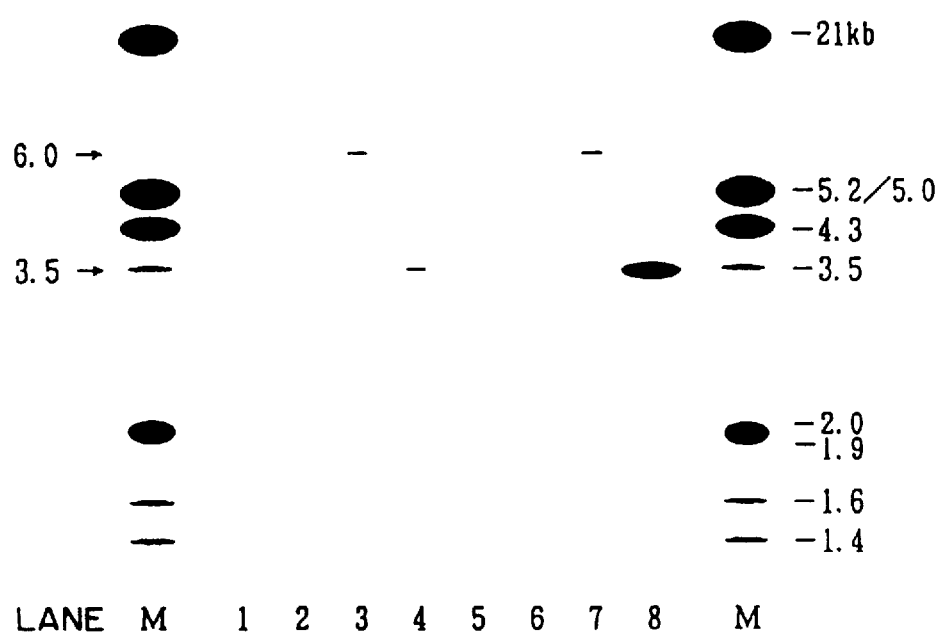
FIG. 1 shows the results obtained by transfecting COS-1 cells or CV-1 cells with combinations of various recombinant adenoviral vectors, recovering DNAs from the transfected cells, digesting the recovered DNA with Hind III, fractionating the DNA fragments by subjecting the treated DNAs to electrophoresis and analyzing by Southern blotting. In the figure, symbols denote as follows.

Lane M: Molecular marker;

Lane 1: CV-1 cells added with medium only;

Lane 2: CV-1 cells transfected with the combination of an adenoviral vector deleted of E3, E1A and E1B regions and having no foreign gene and a recombinant adenoviral vector constructed in Example 1 wherein recombinase Cre gene and CAG promoter have been inserted therein;

Lane 3: CV-1 cells transfected with the combination of an adenoviral vector AdexlLCAHBsSL constructed in Example 2 with an adenoviral vector deleted of E3, E1A and E1B regions and having no foreign gene;

Lane 4: CV-1 cells transfected with the combination of the vector Adex1LCAHBsSL with the recombinant adenoviral vector constructed in Example 1 wherein recombinase Cre gene and CAG promoter have been inserted therein;

Lane 5: COS-1 cells transfected in the same way as in Lane 1;

Lane 6: COS-1 cells transfected in the same way as in Lane 2;

Lane 7: COS-1 cells transfected in the same way as in Lane 3;

Lane 8: COS-1 cells transfected in the same way as in Lane 4.

DETAILED DESCRIPTION OF THE INVENTION

The present invention will be described below in more detail.

The DNA viral vector used in the present invention may be any vectors derived from DNA virus such as an adenovirus that can exist only extrachromosomally after infection. Such DNA virus-derived vectors may be used without any restriction. Examples of such vectors include an adenoviral vector, a vaccinia viral vector and a papovaviral vector.

Hereinafter, the present invention will be described with reference to an adenoviral vector which is a preferred example of the DNA viral vector for transfecting an animal cell and which bears a recombinase gene or a recombinase-recognizing-sequence.

The adenovirus used in the present invention is an adenovirus which utilizes an animal as a natural host, and a particularly preferred adenovirus is a human adenovirus utilizing a human as a host. Human adenoviral genome is a double-stranded linear DNA of about 36 kbp, and has a unique structure in that the DNA strand has an inverted repeat sequence of about 100 bp at both ends and that the DNA strand further has two 55 k proteins which are processed from the E2B gene product and which are covalently bound to the 5' end of both ends of the DNA strand.

The genome of the adenovirus used in the present invention is deleted at the E1 region, especially the E1A region. This is because, by being deleted at the E1A region which is associated with a neoplastic ransformation activity of adenovirus, the adenovirus is endered non-virulent and only a foreign gene integrated in the genome is selectively expressed. The entire E1A region is not necessarily deleted, but the deletion of the partial E1A region only, especially the 1.3 to 9.3% segment only in the E1A region may attain the desired purpose as stated above.

Furthermore, the genome in the adenovirus used in the present invention may also be deleted of the E3 region. In particular, the deletion of 79.6 to 84.8% segment in the E3 region is preferable, because the segment is not essential for replication of the adenovirus.

Therefore, the adenovirus used in the present invention is characterized in that the adenovirus cannot propagate in usual host cells, except for a human fetal kidney-derived cell line (293 cell line) wherein the E1A and E1B genes are persistently expressed.

The recombinant adenoviral vector particles used in the present invention can proliferate in the 293 cell line at a titer level as high as $10^8$ to $10^9$ pfu (plaque forming unit)/ml, which is the same as in wild cell strains. When transfected into other cells or animal tissues, the virus particles invade into cells highly efficiently and the virus genome is transferred to the nucleus. However, the adenovirus vector lacks the E1A gene, and native adenoviral promoters in the vector which are activated by the EIA gene product can not become to be operable. On the other hand, the foreign gene integrated into the adenoviral genome can be transcribed by the foreign promoter which has also been integrated in the adenoviral genome. Accordingly, the recombinant adenovirus particles used in the present invention can minimize adverse affects caused by a native adenoviral genome, and the foreign gene in the recombinant adenovirus vector can be expressed efficiently in various kinds of animal cells.

Although human adenovirus wild strains can propagate only in human cells after infection, the foreign gene in the recombinant adenovirus of the present invention can be expressed in a much wider range of cells and tissues. This is because the recombinant adenovirus of the present invention can function efficiently as an expression vector even in a cell wherein an usual adenovirus can not proliferate, as far as the recombinant adenovirus particles can infect and invade into the cell.

The genome in the recombinant adenovirus of the present invention can not replicate extra-chromosomally and is maintained in the nucleus only for two weeks to two months. Thus, the repeated administrations of the recombinant adenovirus is required for expressing the foreign gene over a long time period. However, the generation of an antibody may be induced upon repeated administration.

According to the present invention, a novel recombinant adenovirus having a recombinase gene is constructed, and on the other hand, another new recombinant adenovirus is also constructed which contains two recombinase-recognizing sequences which are substrates for the recombinase and which further contain an objective foreign gene and an origin of replication, both of which are located between the two recombinase-recognizing sequences.

The two recombinant adenoviruses are co-transfected into an animal cell wherein the recombinase will be expressed. Then, the recombinase acts on the two recombinase-recognizing sequences to cleave then to form a circular DNA molecule. Thus, the formed circular DNA molecule containing the origin of replication and foreign gene can autonomously replicate within the co-transfected cells to continue in the expression of the foreign gene.

As the promoters used in the present invention, there are an animal viral gene promoter and an animal cellular gene promoter. Examples of the animal viral gene promoters include a SV40 gene promoter and an adenovirus major late gene promoter. Examples of the animal cellular gene promoters are a thymidine kinase gene promoter, a metallothionein gene promoter and an immunoglobulin gene promoter. A particularly advantageous promote in the present invention is CAG promoter. The CAG promoter is a hybrid promoter comprising a cytomegalovirus enhancer, a chicken β-actin promoter, and a rabbit β-globin splicing acceptor and poly(A) sequence. The CAG promoter has been reported as a high expression vector in Japanese Patent Application Laid-Open No. 3 (1991)-168087. The CAG promoter may be constructed by cutting out it from a plasmid pCAGGS described in the Laid-Open specification supra at page 13, line 20 to page 20, line 14 and page 22, line 1 to page 25, line 6, with restriction enzymes SalI and Hind III. The thus constructed CAG promoter may be used in the present invention.

The recombinase used in the present invention is a specific DNA recombination enzyme, and capable of recognizing a specific DNA sequence to cleave the sequence and exchanging the resulting DNA fragments therewith to relegate those fragments. As such an enzyme, there is recombinase Cre encoded by bacteriophage P1 of *E. coli*. The substrate for this enzyme is a DNA sequence of loxP in bacteriophage P1 [Abremski et al., J. Biol. Chem., 1984, 1509–1514 and Hoess et al., P.N.A.S., 1984, 81, 1026–1029]. That is, the loxP DNA sequence is a recognition sequence for recombinase Cre. Another example of the recombinase is a recombinase encoded by FLP gene derived from yeast 2 μ-plasmid [James R. Broarch et al., Cell, 29, 227–234]. Furthermore, a recombinase derived from pSR1 plasmid of *Schizosaccharomvces luxii* may also be employed. This recombinase is encoded by R gene [Matsuzaki et al., Molecular and Cellular Biology, 8, 955–962 (1988)]. Among them, bacteriophage Pl-derived recombinase, recombinase Cre, is particularly preferred for the present invention.

The recombinase Cre gene may be prepared by amplifying the sequence coding the recombinase gene in bacteriophage P1 DNA with polymerase chain reaction (PCR). The other recombinase genes may be prepared with the PCR method in a similar manner. Primers used in the PCR method are selected so as to amplify the sequence coding the entire sequence of the recombinase gene. For conveniently constructing the recombinant adenoviral vector, it is preferred to provide the primers with a suitable restriction site at the end of each primer.

The recognition sequence of the recombinase is usually a several tens bp sequence. For example, the loxP sequence is composed of 34 bp, and the nucleotide sequences have been identified by Abremski et al., J. Biol. Chem., 1984, 1509–1514 and Hoess et al., P.N.A.S., 1984, 81, 1026–1029. Accordingly, the recombinase gene may be chemically synthesized in a conventional manner and provided for use in the present invention.

The poly(A) sequence used in the present invention is not particularly limited, but a rabbit β-globin-derived sequence is particularly preferred.

In the present invention, it is advantageous to introduce a nuclear transfer signal sequence together with the recombinase gene into the adenoviral vector. After transfection of the adenoviral vector into cells, the recombinase is transcribed in the nucleus of the cells and then extranuclearly secreted. Thus, in order for the expressed recombinase to act on the recombinase-recognizing sequence in the another adenoviral vector, the recombinase must be transferred to return into the nucleus. The nuclear transfer signal sequence accelerates the transfer of the recombinase into the nucleus [Daniel Kalderon et al., Cell, 39, 499–509 (1984)].

As the origin of replication used in the present invention which is operable in animal cells, there are those derived from virus and animal cells. Examples of the virus-derived origin of replication include those derived from papovavirus, herpes virus, adenovirus, pox virus and parvovirus. As the papovavirus-derived origin of replication, there is an origin of replication derived from SV40.

These origins of replication are introduced into the recombinant adenoviral vector of the present invention, whereby the circular DNA molecule cut out by the recombinase can autonomously replicate in the transfected cells.

The foreign gene used in the present invention is not particularly limited, as long as the gene is expressed under control of the hybrid promoter (CAG promoter) described above or other promoters. In view of practical utility, preferred examples include normal genes which are defectiveden patients such as adenosine deaminase, dystrophin, low density lipoprotein receptor, α-1 antitrypsin, blood coagulation factor VIII or blood coagulation factor IX, and galactosidase α or β; cytokines such as interleukins 1 through 12, interferon-α, β or γ, tumor necrosis factor-α or β, granulocyte colony stimulating factor, granulocyte macrophage colony stimulating factor, erythropoietin, growth hormone, insulin and insulin-like growth hormone; neurotrophic factors; non-self antigen genes such as allo-HLA (HLA-B7); nucleotide sequences encoding a viral antigen; an antioncogene such as p53, RB, WT–1, NM23 and NF–1; an antisense of oncogene such as Ras sequence; and suicide genes such as thymidine kinase and cytosine deaminase.

The origin of replication, promoter, foreign gene and poly(A) sequence are inserted between the two recombinase-recognizing sequences in the adenoviral vector, and generally located in this order from the upstream one of the two recombinase-recognizing sequences.

However, the foreign gene, poly(A) sequence, origin of replication and promoter may also be located in this order from the upstream one of the two recombinase-recognizing sequences. Once they have been included in a circular DNA molecule formed from the adenoviral vector by the recombinase, the above two orders can not be distinguished from each other.

When applying the present invention to gene therapy, an animal cell is co-transfected with both the recombinant adenoviral vector expressing the recombinase and the recombinant adenoviral vector bearing the two recombinase-recognizing sequences and further bearing the promoter, foreign gene and poly(A) sequence, each of which is located between the two recombinase-recongnizing sequences. The transfections of the two vectors may be carried out simultaneously or sequentially, because the DNA vectors transferred into the animal cells persist stably over more than one month.

After being co-transfected into the cell, the recombinant adenoviral vector expressing the recombinase continues to express the recombinase for a certain period of time, whereby the recombinase is continuously produced. The produced recombinase acts on the co-transfected recombinant adenoviral vector bearing the two recombinase-recognizing sequences to cut out the DNA fragment located between the two recombinase-recognizing sequences to form a circular DNA molecule. The circular DNA molecule has the origin of replication which is operable in animal cells, and therefore autonomously replicates in the co-transfected cells to continue expressing the foreign gene. Accordingly, only the single co-transfection of the two adenoviral vectors can almost permanently continue exhibiting the desired therapeutic effect. It is thus believed that the recombinant adenovirus vectors of the present invention would be extremely effective for gene therapy.

The gene therapy according to the present invention may be applied in a wide range of human and animal cells such as highly differentiated human and mammal nervous system cells, muscular system cells, hepatic cells, undifferentiated epithelial cells and fibroblast cells.

Hereunder, processes for constructing the recombinant adenoviruses of the present invention are explained below.

1. Firstly, the process for constructing the recombinant adenoviral vector bearing the promoter, recombinase gene and poly(A) sequence is explained below.

It is extremely difficult to construct the recombinant adenoviral vector of the present invention, because the adenoviral genome has proteins covalently linked to both ends thereof, as described herein-above.

Therefore, the following procedures are preferably used in the present invention, with reference o recombinase Cre gene as the recombinase gene. The procedures are also applicable to the other recombinase genes in a similar manner.

(1) Recombinase Cre gene amplified with a PCR method and a plasmid pUC19 (Takara Shuzo Co., Ltd., Japan) are simultaneously digested with restriction enzymes Pst I and XbaI (Takara Shuzo Co., Ltd., Japan). The resulting products are mixed and ligated to obtain a plasmid pUCCre having the recombinase Cre gene introduced therein.

(2) A cassette cosmid pAdexlCAwt bearing CAG promoter, which has been prepared by a method described in SAIBO KOGAKU (Cell Engineering), 13, 760–763 (1994), is digested with restriction enzyme SwaI (Boehringer, Germany). The digested product is mixed with the product obtained by digesting the plasmid pUCCre with restriction enzymes PstI and XbaI (Takara Shuzo Co., Ltd., Japan), followed with filling in with Klenow enzyme (Takara Shuzo Co., Ltd., Japan). Then, the DNA fragments are precipitated and ligated with T4 DNA ligase to obtain a cassette cosmid having the recombinase Cre gene introduced therein.

Where promoters other than CAG promoter are employed, firstly from the entire length of the adenoviral genome (36 kb), a cassette cosmid is prepared bearing an about 31 kb genomic DNA deleted of the E3 region (1.9 kb), which is not essential for replication, and the E1A.E1B region (2.9 kb). On the other hand, a plasmid containing a promoter, recombinase Cre gene and poly(A) sequence is prepared, and the plasmid is digested with a suitable restriction enzyme to obtain a recombinase Cre gene expression unit. The expression unit is inserted at the E1A.E1B-deleted site of the adenoviral genome to obtain a cassette cosmid.

(3) The thus obtained cassette cosmid is subjected to an in vitro packaging using lambda in vitro packaging kit Gigapack XL (Stratagene Co., Ltd., U.S.A.).

(4) On the other hand, an adenovirus DNA-protein complex (Ad5dlX DNA-TPC) is prepared. As an adenoviral DNA, a vector Ad5dlX (I. Saito et al., J. Virology, vol. 54, 711–719 (1985)) is used. The vector Ad5dlX is infected to HeLa cells at the amount of 10 Roux tubes, followed with culture. The viral particles are recovered, treated with guanidine hydrochloride and subjected to ultracentrifugation to separate and recover the DNA-TPC complex.

The thus obtained Ad5dlX DNA-TPC complex is treated with a sufficient amount of EcoT22I for preparing the recombinant adenovirus in the following step.

(5) As the final step, the cassette cosmid having the recombinase Cre gene introduced therein is mixed with the Ad5dlX DNA-TPC complex previously treated with EcoT22I, and the resulting mixture is transfected into 293 cells using Celfect kit (Pharmacia) according to a calcium phosphate method. From the dead cells due to propagation of the transfected virus, the viral solution is recovered to obtain the recombinant adenoviral vector bearing the promoter, recombinase gene and poly(A) sequence.

2. Described below is a process for constructing the other recombinant adenoviral vector bearing two recombinase-recognizing sequences and further an origin of replication, a promoter, a foreign gene and a poly(A) sequence, each of which is located between the two recombinase-recognizing sequences. For convenience, the process is described below using the origin of replication of SV40.

(a) Firstly, a cassette cosmid expressing a desired foreign gene is constructed.

(1) A plasmid pCAWG is prepared by inserting SwaI linker into a plasmid pCAGGS bearing CAG promoter (Niwa et al., Gene, 108, 193–200, 1990) at the cloning site. The plasmid pCAWG is digested with SwaI, followed with the treatment of alkaline phosphatase. Then, the desired foreign gene is mixed with the resulting pCAWG and treated with ligase. Using the product, *E. coli* DHI strain (ATCC 33849) is transformed to obtain a plasmid wherein the foreign gene is expressed under control of CAG promoter.

(2) A DNA fragment bearing a foreign gene expression unit wherein the foreign gene is expressed under control of CAG promoter, as well as a SV40 origin of replication is prepared. The plasmid obtained in the above (1) is digested with restriction enzymes SapI and SalI, filled in with Klenow enzyme, and then subjected to electrophoresis to obtain the desired DNA fragment. The recovered DNA fragment is mixed with a plasmid pUC18 (Takara Shuzo Co., Ltd, Japan) previously digested with restriction enzyme SmaI, and then treated with an alkaline phosphatase. The resulting product is treated with ligase to obtain a plasmid having the foreign expression unit and the origin of replication of SV40.

(3) In order to add loxp sequence to the both ends of the DAN fragment containing the expression unit and the origin of replication of SV40, the following procedures are carried out.

A plasmid pUC119 (Takara Shuzo Co., Ltd., Japan) is digested with restriction enzyme Ecl136II. After treating with alkaline phosphatase, the digested plasmid is ligated with a synthetic DNA fragment (SEQ ID NO: 3) bearing loxp sequence which has MluI site and XhoI site at the ends and which is designed so as to form NruI site from each of MluI and XhoI sites after ligation. Thus, a plasmid is obtained which contains the two synthetic DNA fragments inserted therein.

After this plasmid is digested with restriction enzyme NruI and treated with alkaline phosphatase, the treated plasmid is ligated with a DNA fragment obtained by digesting the plasmid constructed in the above (2) with restriction enzymes SalI and Ecl136II and then filled in. Thus, a plasmid is obtained which bears a DNA fragment containing the foreign gene expression unit and the origin of replication of SV40 and further containing the loxP sites at the both ends.

(4) Thereafter, the following procedures are carried out, in order to obtain a recombinant cosmid bearing the DNA fragment containing the foreign gene expression unit and the origin of replication of SV40 and further containing the loxP sites at the both ends.

Firstly, the plasmid obtained in the above (3) is digested with restriction enzymes SmaI and EcoRI and filled in with Klenow enzyme. The product is purified on electrophoresis to prepare a DNA fragment which contains the foreign gene expression unit and the origin of replication of SV40 and which further contains the loxP sites at the both ends. On the other hand, a vector pAdexlcw [SAIBO KOGAKU (Cell Engineering), 13, 760–763, 1994] is digested with restriction enzyme SwaI. The above prepared fragment and the cassette cosmid are mixed and precipitated. The DNA mixture is ligated with T4 DNA ligase to obtain a cassette cosmid containing the fragment bearing the DNA fragment which contains the foreign gene expression unit and the origin of replication of SV40 and which further contains the loxP sites at the both ends.

(b) A construction of recombinant adenoviral vector which has a fragment containing two loxP sequences and further containing an origin of replication, CAG promoter and a foreign gene, each of which is located between the two loxP sequences.

The recombinant adenoviral vector of the present invention can be prepared in the same way as the methods in the above 1. (3) to (5)

The recombinant adenoviral vector bearing the promoter, recombinase gene and poly(A) sequence and the recombinant adenoviral vector bearing the origin of replication of SV40, foreign gene expression unit and loxP sequence at the both ends may be effectively used for the treatment of various diseases including genetic diseases. In more detail, a high titer viral solution containing the two recombinant adenoviral vectors according to the present invention is appropriately diluted, and the diluted solution may be administered through an appropriate route, e.g., topically (central nervous system, portal vein), orally (using enteric coating), by inhalation, subcutaneously, and the like.

Hereinafter, the present invention will be described in more detail by referring to Examples and Reference Examples, but the invention is not to be limited thereto.

In the Examples, various procedures for manipulating phages, plasmids, DNAs, various enzymes, *E. coli*, culture cells and the like were carried out, unless otherwise indicated, according to modifications of the methods as described in Molecular Cloning, A Laboratory Manual, edited by T. Maniatis et al., second edition (1989), Cold Spring Harbor Laboratory. DNA restriction enzymes and modified enzymes were purchased from Takara Shuzo Co., Ltd., New England Biolabs (NEB), Stratagene or Boehringer, and used in accordance with their instructions.

EXAMPLE 1

Construction of recombinant adenoviral vector bearing recombinase Cre gene and CAG promoter
(1) Construction of cassette cosmid for expressing recombinase Cre gene 1) A PCR reaction was conducted using *E. coli* phage P1DNA containing recombinase Cre gene (ATCC 11303-B23) as a template, the following oligonucleotide (SEQ SEQ. ID. NO: 1) as a 5'-primer, the following oligonucleotide (SEQ ID NO: 2) as a 3'-primer, and Vent$^R$ (NEB) as a polymerase. The detailed conditions for the PCR reaction are described below. The product was subjected to electrophoresis on an agarose gel, and a band indicating about 1 kb was excised from the agarose gel to obtain an about 1 kb DNA fragment bearing recombinase Cre gene.

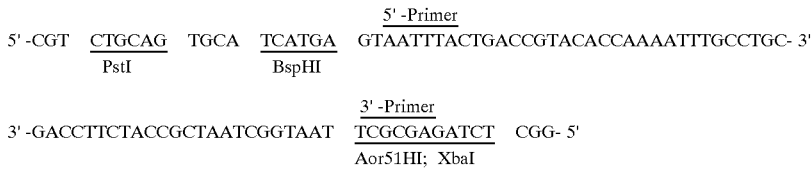

The underlined denotes the recognition site of restriction enzymes.
Conditions for PCR
Buffer: 10 mM KCl, 20 mM Tris-HCl (pH 8.8), 10 mM (NH$_4$)$_2$SO$_4$, 2 mM MgSO$_4$, 0.1% Triton X-100 (buffer offered from NEB was used)
Polymerase: 2 units
dNTP: 400 μM
Primer: 1 μM
P1 phage DNA: 1 ng
Temperature for diassociating double strand: 1.5 minutes
Temperature for annealing: 1.5 minutes
Temperature for chain extension reaction: 2.0 minutes
Reaction cycle: 20 times After each of the thus obtained DNA fragment and pUC19 (Takara Shuzo Co., Ltd., Japan) was digested with restriction enzymes PstI (Takara Shuzo Co., Ltd., Japan) and XbaI (Takara Shuzo Co., Ltd., Japan), the digested products were recovered, and the products from the DNA fragment and that from pUc19 were mixed with each other in a molar ratio of approximately 3:1. The mixture was then ligated using T4 DNA ligase (Takara Shuzo Co., Ltd., Japan). The reaction mixture was used to transform *E. coli* JM109 strain (ATCC 53323). The treated *E. coli* cells were inoculated on LB agar plate supplemented with 100 μg/ml ampicillin, and the transformants growing on the agar were selected to obtain a plasmid pUCCre bearing recombinase Cre gene.

Next, a cassette cosmid pAdexlcAwt containing CAG promoter, which had been prepared according to the method as described in SAIBO KOGAKU (Cell Engineering), 13, 760–763 (1994), was digested with SwaI. Then, 1 μg of the digested product was mixed with 0.1 μg of about 1 Kb DNA fragment obtained by digesting the plasmid pUCCre with PstI and XbaI and filling in with Klenow enzyme (Takara Shuzo Co., Ltd., Japan).

The CAG promoter used herein is disclosed as a high expression vector in Japanese Patent Application Laid-Open No. 3 (1991)–168087. The CAG promoter may be prepared by excising from a plasmid pCAGGS described in the Laid-Open specification supra at page 13, line 20 to page 20, line 14 and page 22, line 1 to page 25, line 6, with restriction enzymes SalI and Hind III. The thus prepared CAG promoter may be used in the present invention.

2) Ethanol was added to the mixture obtained in the above to precipitate the cosmid. The precipiates were recovered by centrifugation, and dissolved in 5-fold diluted TE solution (10 mM Tris-HCl (pH 7.5), 1 mM EDTA).

3) The resulting solution containing the cosmid was subjected to ligation reaction overnight in a final volume of 7 μl, with ATP and T4 DNA ligase in a buffer solution. Sterilized water and a buffer solution for SwaI reaction were added thereto to make the whole volume 48 μl. Then, the ligase was inactivated with heating at 70° C. for 10 minutes.

Unlike a plasmid, a cosmid may usually efficiently package macromolecular DNA which has been formed by linking with each other in a linear tandem form instead of a cyclic form.

4) After adding 2 μl of SwaI (Boehringer, Germany), the digestion of the cosmid was carried out at 25° C. for an hour. The reasons why the cosmid was digested with SwaI are given below.

If a cassette cosmid is religated without the inclusion of an expression unit therein, a SwaI recognition site will be regenerated. Thus, the digestion with SwaI can recleave the cosmid having no expression unit included therein, resulting in that no colony is formed. This is a potential method for selecting only a cassette cosmid having an insert sequence.

5) The cassette cosmid was subjected to phenol extraction, centrifugation and gel filtration according to a conventional method as described in Molecular Cloning, vol. 3, E.34.

6) The digestion with SwaI was carried out again. That is, 5 μl of SwaI was added to the buffer for the SwaI reaction to cleave the cosmid at 25° C. for 2 hours. The cleavage was conducted for the reasons as explained above.

7) The resulting cosmid (1 μl) was subjected to in vitro packaging.

That is, a lambda in vitro packaging kit, Gigapack XL (Stratagene Co., Ltd., U.S.A.) was used in a ¼ scale and the balance was frozen at −80° C. Since Gigapack XL provides a low package efficiency for a cosmid of 42 kb or less, the kit can select to a certain extent a cosmid having become a larger size by including an insert sequence. In this experiment, when 10 colonies were picked up, most of them included the insert sequence. Therefore, the clone having the desired orientation (i.e., the left direction which means the direction from E3 gene region to E1 gene region) could be readily obtained.

The cosmid was manipulated according to a conventional method as described in Izumu Saito et al., JIKKEN IGAKU (Experimental Medicine), vol. 7, 183–187 (1989).

8) The packaged cosmid was infected into *E. coli* strain DH1 (ATCC 33849).

That is, the cosmid was inoculated on each of three Ap+ agar plates (supplemented with ampicillin) and 5 ml of Ap+ LB (pool) in amount of each of ⅟200, ⅟20, ½ and the balance, followed with incubation overnight.

The miniprep DNA from the pool was extracted and prepared. A ratio of the cosmid having the insert sequence was examined according to whole enzymatic digestions. The colony was picked up together with the agar plate, and cultured in 1.5 ml of Ap+ LB overnight to prepare the miniprep DNA.

9) The orientation and structure of the expression unit included in the cosmid were confirmed with digestions with restriction enzymes.

That is, a plasmid bearing the expression unit but deleted of most adenovirus DNA was prepared with NruI and ligase, and a DNA fragment was then prepared from the plasmid for final confirmation of cDNA cloning.

(2) Preparation of adenoviral DNA-protein complex (Ad5 dlX DNA-TPC)

1) As an adenovirus DNA, a vector Ad5 dlX (I. Saito et al., J. Virology, vol. 54, 711–719 (1985)) was used. The vector Ad5 dlX DNA was infected into HeLa cells at the amount of Roux 10 tubes, followed with incubation.

That is, the viral solution (~$10^9$ PFU/ml) of Ad5-dlX was infected at the amount of 0.2 ml/Roux tube. Three days later, the cells peeled off were collected with centrifugation at 1500 rpm for 5 minutes. Most of the adenovirus particles did not exist in the medium, but in the nucleus, and the virus was therefore advantageously purified from the infected cells.

The following procedures were aseptically performed.

2) The thus obtained cells were suspended in 20 ml of 10 mM Tris-HCl (pH 8.0) and sonicated at 200 W for 2 minutes (30 seconds×4) using a sealed type sonicator to destroy the cells thereby to release the virus.

In order to release the virus from the cells, when the cell suspension has the volume of 5 ml or less, five repetitions of freeze-thawing are sufficient. However, when having a larger volume, a sonicator is advantageous for releasing the virus. In this case, a sealed type sonicator with an exclusive cup must be used. An ordinary throw-in type is dangerous, even if the operation is performed in a safety cabinet.

3) After the thus obtained cell debris was removed by centrifugation at 10 k rpm for 10 minutes, the supernatant was overlaid on 15 ml of cesium chloride solution (specific gravity of 1.43) charged in a ultracentrifuging machine (SW28 tube), followed with concentration by centrifugation (25 k rpm, an hour, 4° C.).

4) The virus band immediately below the interface was transferred to a SW50.1 tube. The virus phase immediately below the interface was visually observed, and 5 ml of the virus band was collected. At the same time, another tube was filled up with the cesium chloride solution (specific gravity of 1.34).

These tubes were centrifuged at 4° C. overnight at 35 k rpm. Thenr the thus formed band indicating virus was collected, and transferred onto a tube which previously formed gradients. The tube was further subjected to ultracentrifugation at 4° C. for 4 hours at 35 k rpm.

5) The band indicating virus was collected, and mixed with a same amount of 8M guanidine hydrochloride. Furthermore, 4M guanidine hydrochloride-saturated cesium chloride was added to the mixture. The resulting mixture was filled in a VTi65 tube. The particle protein was denatured with 4M guanidine hydrochloride to cause dissociation, whereby the DNA-TPC complex was released. Ethidium bromide could not be used in this experiment, because any procedure for removing the ethidium bromide used has not yet been established.

6) The tube described above was subjected to ultracentrifugation at 15° C. overnight at 55 k rpm, followed with fractionation with 0.2 ml. From each of the fractions, 1 μl was picked up, and mixed with 1 μg/ml of ethidium bromide aqueous solution to confirm the presence or absence of a DNA with fluorescence-staining. Two to three fractions containing a DNA were collected.

7) The fractions were twice dialyzed against 500 ml of TE overnight and were then stored at −80° C. The amount of the thus obtained Ad5dlX DNA-TPC complex as determined on the basis of $OD_{260}$ value in they as in conventional method.

8) The resulting Ad5dlX DNA-TPC complex was digested with a sufficient amount of EcoT22I for 2 hours, and then stored at −80° C. for constructing recombinant adenoviral vector at the following third step.

In the meantime, the DNA-TPC complex could undergo digestion with restriction enzymes, dialysis and gel filtration, but failed to undergo electrophoresis, phenol treatment and ethanol precipitation. The cesium chloride equilibrium centrifugation only is available as a concentration method. Therefore, the DNA-TPC complex system was maintained at a concentration as high as possible. Approximately 300 μg of the DNA-TPC complex could be obtained from the infected cells of 10 Roux tubes.

9) An aliquot of the DNA-TPC complex solution was collected, and 10 μl of BPB buffer for electrophoresis was added thereto. Then, 1 μl of proteinase K (10 mg/ml) was added to the mixture. The resulting mixture was incubated at 37° C. for 10 minutes to digest the terminal protein in the DNA-TPC complex. After phenol extraction, the supernatant was separated by electrophoresis on an agarose gel to confirm the completion of digestion.

After the restriction enzyme buffer in the EcoT22I-digested DNA-TPC was removed by centrifugational gel filtration, the resulting products were separately charged in tubes and stored at −80° C.

3) Isolation of recombinant virus and preparation of high titer viral solution

1) Each one of 6 cm and 10 cm diameter Petri dishes was charged with the 293 cell lines cultured in DME supplemented with 10% FCS.

2) After 8 μg (3 to 9 μg is appropriate) of pAdexlW DNA having the expression unit introduced therein was mixed with 1 μg of Ad5dlX DNA-TPC complex previously digested with EcoT22I, the resulting mixture was transfected into the 293 cell lines on the 6 cm Petri dish using Celfect Kit (Pharmacia) according to a conventional calcium phosphate method. That is, the mixture was dropped onto the medium in the 6 cm Petri dish, and the incubation was continued.

After the overnight incubation (for about 16 hours), the culture medium was exchanged the next morning. Then, in the evening, the medium containing cells was poured at the amount of 0.1 ml/well with 5% FCS-containing DME into wells in three 96-well collagen coated plates (non-diluted, 10-fold diluted, 100-fold diluted). In order to avoid a significant difference in the cell count between each plate, one third of the 293 cells harvested from 10 cm Petri dish were added on each of two diluted solution plates.

3) Three to four days after and eight to ten days after, 50 μl of 10% FCS-containing DME was further added to each well. When the 293 cell lines got thin, 10% FCS-containing DME was earlier added to the well.

The wells, wherein the virus propagated and the cells were dead, were observed in 7 to 15 days. From every well wherein the cells were completely dead, the culture media containing dead cells was transferred with a sterile pasteur pipette into a 1.5 ml sterilized tube. The tube was quickly frozen and stored at −80° C.

4) The observation was finished in 15 to 18 days. About ten (10) tubes were selected from the tubes charged with the culture media containing the cells which were dead at a relatively late stage. After six (6) repetitions of the freeze-thawing, centrifugation was conducted at 5 k rpm for 10 minutes. The resulting supernatant was stored as a first seed at −80° C.

The wells in which the virus started to propagate at an earlier stage suggest a higher probability of mixed infections with a plurality of virus strains.

5) The 293 cell lines were charged in a 24-well plate, and 5% FCS-DME (0.4 ml/well) and 10 μl of the first viral seed were added to wells in duplicate.

6) Where the cells were completely dead in about 3 days, the supernatant was obtained from one of the duplicate wells by six (6) repetitions of freeze-thawing and centrifugation in a manner similar to the procedures for preparing the first viral seed as described above. The thus obtained supernatant was stored at −80° C. for use as a second seed. The titer of the second viral solution was approximately $10^7$ to $10^8$ PFU/ml. The dead cells in another well of the duplicate wells were centrifuged at 5 k rpm for 5 minutes, and the supernatant was discarded. The cells alone were stored at −80° C. (cell pack). The cell packs of 10 viral strains were collected, and the entire DNA was extracted from the infected cells according to the following procedures. To each cell pack were added 400 μl of TNE (50 mM Tris-HCl, pH 7.5, 100 mM NaCl, 10 mM EDTA), 4 μl of proteinase K (10 mg/ml) and 4 μl of 10% SDS.

7) After treating at 50° C. for an hour, twice extractions with phenol-chloroform, twice extractions with chloroform and then ethanol precipitation were performed. The nucleic acid recovered by ethanol preparation was dissolved in 50 μl of TE containing 20 μg/ml ribonuclease.

After 15 μl of the solution was digested with XhoI, which recognizing site contains CG, the digested product was subjected, together with the XhoI-digested product of an expression cosmid cassette, to electrophoresis overnight on agarose gel having a length of about 15 cm. The patterns thus obtained were compared. The clone which has a band indicating accurately the DNA sequence from the cleavaged site in the expression unit to the left end of the adenovirus genome was selected. The clones which provided many bands indicating undetermined DNA sequences were discarded, since there was a possibility that the clones would be contaminated with the virus having deletions.

An adenovirus DNA generally propagates at a level of 10,000 copies/cell. Accordingly, even a whole DNA could be extracted including a native cellular DNA and adenoviral DNA, digested with restriction enzymes and then subjected to electrophoresis, thereby to observe bands indicating DNA fragments derived from the adenoviral DNA. The restriction enzyme such as XhoI containing CG in the recognition site does not digest the cellular DNA. As a result, when loaded on electrophoresis, the patterns could be readily observable and distinguishable. When using other enzymes, the non-infected 293 cell line DNA was required as a control because there is a generation of human cell repeated sequences. The digested non-infected 293 cell line DNA was subjected to electrophoresis to observe bands which would indicate human cell repeated sequences.

8) The second seed solution, which was confirmed by the XhoI digestion, was transfected at an amount of 0.1 ml into the 293 cell lines charged in a 150 cm² collagen-coated bottle containing 25 ml of medium.

When the cells were dead in three days, the culture medium containing dead cells was treated aseptically with a sealed type sonicator at the maximum output of 200 w for 2 minutes (30 seconds×4) to release the virus.

The precipitates were removed by centrifugation at 3 k rpm for 10 minutes at 4° C., and the obtained supernatant was charged at an amount of 2 ml in each of 13 tubes of 5 ml freezing tube. The tubes were quickly frozen with dry ice and stored at −80° C. to prepare a third seed solution. The third seed solution which contains the recombinant adenoviral vector of the present invention showed a titer as high as $10^9$ PFU/ml.

After transfecting 5 μl of the third seed solution into one well containing the 293 cell lines in a 24-well plate, the propagated viral DNA was digested with restriction enzymes and then subjected to electrophoresis. The resulting patterns were confirmed by the procedures as described hereinabove. Where there was any doubt that the virus would be possibly mixed with the deleted virus or the parent virus, all of the third seeds were discarded. This is because there would be a possibility that the deleted virus, which had already existed in the second viral solution, rapidly propagated at an appreciable level. Therefore, the above procedures were again performed with another second seed solution. Alternatively, the virus solution was purified by subjecting the first seed solutions to a limiting dilution method.

Reference Example

Simple assay for the titer of the recombinant adenoviral vector of the present invention The recombinant adenoviral vector according to the present invention may be assayed for the titer in a simple manner according to the following procedures.

(1) One 10 cm diameter Petri dish charged with the 293 cells is prepared.

The recombinant adenoviral vector solution (i.e., the third seed solution) is serially diluted to $10^{-1}$ to $10^{-4}$ using 5% FCS-supplemented DME. For example, 0.9 ml of DME and 0.1 ml of the virus solution are used to prepare the solution. The micropipette tips are all exchanged.

(2) In all wells of one collagen-coated 96-well plate, 5% FCS-supplemented DME is charged by 50 μl each.

In 8 wells on the first lane, 25 μl each of the recombinant adenoviral vector solution diluted to $10^{-4}$ is charged.

Using a multi-channel pipette for a 8-well plate, 25 μl of the vector solution is transferred to the wells on the second lane. Thereafter, the same operation is repeated until the 11th lane, and the last 25 μl of the vector solution is discarded. As the result, the $3^n$ serial diluted solutions may be prepared until $3^{11} \times 10^{-4}$. The solution in the 12th lane is non-infected cells as a control.

Tips used in this experiment are exchanged every uses.

EXAMPLE 2

Construction of recombinant adenoviral vector bearing two loxP sequences and further bearing origin of replication of SV40, CAG promoter and hepatitis B virus surface antigen (HBs), each of which is located between the two loxP sequences (1) Construction of cassette cosmid for expressing hepatitis B virus surface antigen (HBs)

1) A plasmid pHBVadr4 having HBs CDNA (Fujiyama et al., Nucleic Acids Res., 11, 4601–4610, 1983) was digested with restriction enzymes Psp1406I and XhoI, followed with filling in with Klenow enzyme. The resulting digested plasmid was subjected to electrophoresis on an agarose gel to recover a 710 bp DNA fragment.

2) The following procedures were carried out to obtain an expression unit for expressing HBs cDNA under control of CAG promoter.

By inserting SwaI linker into the cloning site in a plasmid pCAGGS containing CAG promoter (Niwa et al., Gene, 108, 193–200, 1990), a plasmid pCAWG was produced. The plasmid pCAWG was digested with SwaI, followed with the treatment of alkaline phosphatase. Then, the resulting product was mixed with the 710 bp DNA fragment obtained in the above 1) in a molar ratio of approximately 1:3. The mixture was ligated using T4 DNA ligase. *E. coli* DHI strain (ATCC 33849) was transfected with the reaction mixture. The transformants were picked up from LB agar plate supplemented with ampicillin. A plasmid pCAG.HBs was obtained wherein the 710 bp DNA fragment has been correctly inserted in such a way that HBs cDNA is expressed under control of CAG promoter.

3) The following procedures were carried out, in order to obtain a DNA fragment containing the HBs expression unit and the origin of replication of SV40.

The plasmid pCAG.HBs was digested with SapI and SalI, followed with filling in with Klenow enzyme. Then, the resulting product was subjected to electrophoresis on an agarose gel to recover a 3.6 kb DNA fragment. A plasmid pUC18 (Takara Shuzo Co., Ltd., Japan) was digested with restriction enzyme SmaI and treated with alkaline phosphatase, and then mixed with the 3.6 kb DNA fragment in a molar ratio of approximately 1:3. The mixture was ligated to obtain a desired plasmid pUC18CAHBsS.

4) Next, the following procedures were carried out, in order to add loxP sites into the both ends of the DAN fragment bearing the HBs expression unit and the origin of replication of SV40.

A plasmid pUC119 (Takara Shuzo Co., Ltd., Japan) was digested with restriction enzyme E1136II, and treated with alkaline phosphatase. The resulting product was ligated with the following synthetic DNA fragment (SEQ ID NO: 3) bearing loxP sequence which had MluI site and XhoI site at the ends and which was designed so as to form NruI site from each of MluI and XhoI sites after ligation. Thus, a plasmid pULL2r was obtained wherein the two synthetic DNA fragments were inserted therein.

Synthetic DNA Fragment

5'-CGAACGCGTATAACTTCGTATAGCATACATTATAC GAAGTTATCTCGAGTCG-3'
3'-GCTTGCGCATATTGAAGCATATCGTATGTAATATG CTTCAATAGAGCTCAGC-5'

The underlined sequence denotes the loxP site.

The pUC18CAHBsS obtained in the above 3) was digested with restriction enzymes SalI and Ec1136II. After the digested product was filled in with Klenow enzyme, the resulting product was subjected to electrophoresis on an agarose gel, and 3.6 kb DNA fragment was recovered. The plasmid pULL2r was digested with restriction enzyme NruI and then treated with alkaline phosphatase. The thus treated plasmid was ligated with the 3.6 kb DNA fragment to obtain a desired plasmid pULCA.HBsS.

5) The following two DNAs were prepared, in order to obtain a recombinant cosmid bearing a DNA fragment having loxP sites at the both ends which fragment contains the HBs expression unit and the origin of replication of SV40.

(a) The plasmid pULCA.HBsS was digested with restriction enzymes SmaI and EcoRI, followed with rendering the both ends blunt with Klenow enzyme. Then, the product was subjected to electrophoresis on an agarose gel to recover 0.3 μg of a 3.7 kb DNA fragment.

(b) The plasmid pAdexlcw [SAIBO KOGAKU (cell Engineering), 13, 760–763, 1994] was digested with restriction enzyme SwaI to obtain 1 μg of the digested product.

The two DNA products obtained in the above (a) and (b) were mixed, and the mixture was treated in the same way as the procedures of Example 1, (1), 2) through 9) to obtain the desired recombinant cosmid.

The desired recombinant adenoviral vector AdexlLCAH-BsSL bearing the two loxP sequences and further bearing the origin of replication of SV40, CAG promoter and hepatitis B virus surface antigen (HBs), each of which was located between the two loxp sequences, was obtained by the procedures similar to those of Example 1, (2) and (3).

EXAMPLE 3

Infection Experiment

COS-1 cells or CV-1 cells were cultured in a 6 cm diameter Petri dish until the cells covered over the entire bottom surface of the dish.

The adenoviral vectors obtained in Examples 1 and 2 were adsorbed over an hour at m.o.i.=5, according to the following protocol. Three days after, the cells were harvested to be subjected to Southern blotting analysis.

That is, the recombinant adenoviral vector AdexlLCAH-BsSL bears HindIII site of about 6.0 kb and forms a 3.5 kb circular DNA molecule after cleavage with recombinase Cre at the loxP sites. Because this circular DNA molecule has one HindIII site, the recovered DNAs treated with HindIII were analyzed by Southern blotting. A 710 bp HBs fragment was used as a probe.

The results are shown in FIG. 1.

As is clearly seen from FIG. 1, a 3.5 kb linear DNA which was produced by digestion of the circular DNA molecule with HindIII was observed in Lanes 4 and 8, only when transfected with the combination of the two adenoviral vectors obtained in Examples 1 and 2.

When transfected with the adenoviral vector obtained in Example 2 and the adenoviral vector bearing no recombinase Cre gene, the 3.5 kb band was not observed, but only the 6.0 kb band which was generated from AdexlLCAHB-sSL by excision with HindII was observed in Lanes 3 and 7.

Furthermore, comparison in band density between Lanes 7 and 8 reveals that the circular DNA molecule autonomously replicated by 40 times within the transfected COS-1 cells. On the other hand, the fact that the density of Lane 3 was almost the same as that of Lane 4 indicates that the circular DNA molecule did not replicate within CV-1 cells. This is consistent with the fact that the origin of replication derived from SV40 can not function within CV-1 cells.

The foregoing results obviously establish that, when an animal cell is transfected with the combination of the two adenoviral vectors of the present invention obtained in Examples 1 and 2, the DNA fragment located between the two recombinase-recognizing sequences in the vector is excised out to form the circular DNA molecule, and the circular DNA molecule autonomously replicates within the transfected cell.

The infection experiment described above is conveniently carried out as follows.

Where serum in a medium is not FCS (where it is, e.g., CS), the cultured cells are washed twice with serum-free medium.

The viral solution (diluted with serum-free or FCS-supplemented medium) is added during the procedures in such an amount that the cell surface is not dried up. The amount is approximately 30 to 40 μl for a 96-well microplate, 50 to 70 μl for a 24-well microplate and 100 to 200 μl for a 10 cm diameter Petri dish. It is practically advantageous to intentionally retain the medium in a small quantity prior to supplementing to the viral solution, then add the viral solution to the retained medium to make the volume as indicated above.

By shaking the plate several times at a few seconds interval like a seesaw, the viral solution is uniformly spread onto the cells. This operation is carried out 3 times every 20 minutes, and during the operation the cells should be put in a $CO_2$ incubator.

After the third operation is completed (one hour after the transfection), a conventional amount of the culture broth is added to perform a conventional incubation. The time for transfection is generally an hour, and at most, about 2 hours are sufficient for this purpose.

According to the present invention, there are provided recombinant DNA viral vectors which may be transfected into a variety of animal cells in such a way that a foreign gene is able to autonomously replicate within the transfected animal cells. The present invention also provides a simple process for producing the recombinant DNA viral vectors. The recombinant DNA viral vectors of the present invention are useful especially for the treatment of hereditary diseases.

What is claimed is:

1. A recombinant adenoviral vector comprising:

two DNA sequences which serve as a substrate for a recombinase enzyme, an origin of replication which is operable in an animal cell, a promoter, a foreign gene and a poly(A) sequence, wherein said origin of replication, promoter, foreign gene and poly(A) sequence are located between the two DNA sequences, and wherein said vector contains an E1A gene region deletion.

2. A recombinant adenoviral vector according to claim 1, wherein said origin of replication, promoter, foreign gene poly(A) sequence are located in this order from the upstream one of the two DNA sequences which serve as a substrate for said recombinase enzyme.

3. A recombinant adenoviral vector according to claim 1, wherein said foreign gene, poly(A) sequence, origin of replication and promoter are located in this order from the upstream one of the two DNA sequences which serve as a substrate for said recombinase enzyme.

4. A recombinant adenoviral vector according to any one of claims 1, 2 and 3 and wherein said DNA sequence encodes lox P which is a substrate for recombinase Cre.

5. A recombinant adenoviral vector according to any one of claims 1, 2 and 3 wherein said origin of replication is derived from a virus or an animal cell.

6. A recombinant adenoviral vector according to claim 5 wherein said origin of replication is selected from the group consisting of origins of replication derived from papovavirus, herpes virus, adenovirus, pox virus and parvovirus.

7. A recombinant adenoviral vector according to any one of claims 1, 2 and 3, wherein said promoter and poly(A) sequence are involved in a hyprid promoter CAG comprising a cytomegalovirus enhancer, a chicken β-actin promoter, and a rabbit β-globin splicing acceptor and poly(A) sequence.

8. A method for transducing a foreign gene into an animal cell in vitro, which comprises the steps of:

co-transfecting the animal cell with both a recombinant adenoviral vector comprising a promoter, a recombinase gene and a poly(A) sequence, and a recombinant adenoviral vector comprising two DNA sequences which serve as a substrate for a recombinase enzyme, an origin of replication which is operable in said animal cell, a promoter, a foreign gene and a poly(A) sequence, wherein said origin of replication, promoter, foreign gene and poly(A) sequence are located between the two DNA sequences which serve as a substrate for a recombinase enzyme, and wherein said vectors contain E1A gene region deletions;

cutting off a DNA fragment containing said origin of replication, promoter, foreign gene and poly(A) sequence to produce a circular DNA molecule; and autonomously replicating said circular DNA molecule within the co-transfected animal cell.

9. A method for transducing a foreign gene into an animal cell in vitro according to claim 8, wherein said recombinase gene is recombinase Cre gene derived from E. coli P1 phage.

10. A method for transducing a foreign gene into an animal cell in vitro according to claim 9, wherein said DNA sequence which serve as a substrate for a recombinase enzyme is a DNA sequence encoding lox P, wherein lox P is a substrate for recombinase Cre.

11. A method for transducing a foreign gene into an animal cell in vitro according to claim 8 or 10, wherein said origin of replication, promoter, foreign gene and poly(A) sequence are located in this order from the upstream one of the two DNA sequences which serve as a substrate for said recombinase enzyme.

12. A method for transducing a foreign gene into an animal cell in vitro according to claim 8 or 10, wherein said foreign gene, poly(A) sequence, origin of replication and promoter are located in this order from the upstream one of the two DNA sequences which serve as a substrate for said recombinase enzyme.

13. A method for transducing a foreign gene into an animal cell in vitro according to claim 8 or 10, wherein said origin of replication is derived from a virus or an animal cell.

14. A method for transducing a foreign gene into an animal cell in vitro according to claim 13, wherein said origin of replication is selected from the group consisting of origins of replication derived from papovavirus, herpes virus, adenovirus, pox virus and parvovirus.

15. A method for transducing a foreign gene into an animal cell in vitro according to claim 8 or 10, wherein each of said two promoters and poly(A) sequences are involved in a hybrid promoter CAG comprising a cytomegalovirus enhancer, a chicken β-actin promoter, and a rabbit β-globin splicing acceptor and poly(A) sequence.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: Other nucleic acid (optional DNA
        containing partially genomic DNA)

( i i i ) HYPOTHETICAL: YES ( i v ) ANTI-SENSE: NO ( v i ) ORIGINAL SOURCE:
        ( A ) ORGANISM: E. coli phage P1DNA ( i x ) FEATURE:
        ( C ) IDENTIFICATION METHOD: S ( x i ) SEQUENCE DESCRIPTION: SEQ ID NO: 1:

```
CGTCTGCAGT   GCATCATGAG   TAATTTACTG   ACCGTACACC   AAAATTTGCC   TGC                    53
```

( 2 ) INFORMATION FOR SEQ ID NO: 2:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: Other nucleic acid (optional DNA
        containing partially genomic DNA)

( i i i ) HYPOTHETICAL: YES ( i v ) ANTI-SENSE: NO ( v i ) ORIGINAL SOURCE:
        ( A ) ORGANISM: E. coli phage P1DNA ( i x ) FEATURE:
        ( C ) IDENTIFICATION METHOD: S ( x i ) SEQUENCE DESCRIPTION: SEQ ID NO: 2:

```
GGCTCTAGAG   CGCTTAATGG   CTAATCGCCA   TCTTCCAG                                         38
```

( 2 ) INFORMATION FOR SEQ ID NO: 3:

( i ) SEQUENCE CHARACTERISTICS:
        ( A ) LENGTH: 52 base pairs
        ( B ) TYPE: nucleic acid
        ( C ) STRANDEDNESS: double
        ( D ) TOPOLOGY: linear

```
    ( i i ) MOLECULE TYPE: Other nucleic acid (optional DNA
                           containing partially genomic DNA)

( i i i ) HYPOTHETICAL: YES ( i v ) ANTI-SENSE: NO ( v i ) ORIGINAL SOURCE:
              ( A ) ORGANISM: E. coli phage P1DNA ( i x ) FEATURE:
              ( C ) IDENTIFICATION METHOD: S ( x i ) SEQUENCE DESCRIPTION: SEQ ID NO: 3:

CGAACGCGTA  TAACTTCGTA  TAGCATACAT  TATACGAAGT  TATCTCGAGT  CG                       5 2
```